(12) United States Patent
Wilson

(10) Patent No.: US 6,420,556 B1
(45) Date of Patent: Jul. 16, 2002

(54) ACYL ISOTHIOCYANATE RESINS AND THEIR USE IN SOLID-SUPPORTED SYNTHESIS OF GUANIDINES

(75) Inventor: Lawrence Joseph Wilson, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/857,956

(22) PCT Filed: Dec. 15, 1999

(86) PCT No.: PCT/US99/29771

§ 371 (c)(1),
(2), (4) Date: Jun. 12, 2001

(87) PCT Pub. No.: WO00/35860

PCT Pub. Date: Jun. 22, 2000

Related U.S. Application Data

(60) Provisional application No. 60/112,756, filed on Dec. 17, 1998.

(51) Int. Cl.$^7$ .................. C07C 277/08; C07C 331/24; C07C 279/16; C07C 279/10; C07C 279/14

(52) U.S. Cl. .................. 544/166; 546/200; 546/244; 558/17; 558/18; 558/19; 564/230; 564/231; 564/237; 564/238; 525/326.2; 525/327.7; 525/328.3; 525/333.5; 525/333.6; 525/393; 530/345; 530/408

(58) Field of Search .................. 564/230, 231, 564/237, 238; 546/200, 244; 544/166; 558/17, 18, 19

(56) References Cited

U.S. PATENT DOCUMENTS 5,041,388 A    8/1991  Boyd et al.

OTHER PUBLICATIONS

Zaragoza et al., "Resin–bound isothiocyanates and their synthetic equivalents as intermediates for the solid–phase synthesis of substituted thiophenes," J. Org. Chem. 1997, 62, pp. 6096–6097.*

Poss et al., "A mild and efficient method for the preparation of guanidines," Tetrahedron Letters, vol. 33, No. 40, 1992, pp. 5933–5936.*

Robinson et al., "Solid Phase Synthesis of Guanidines", Tetrahedron, vol. 53, No. 19, 1997, pp. 6697–6705.

Kowalski et al., "Solid Phase Synthesis of a Diketopiperazine Catalyst Containing the Unnatural Amino Acid (S)–Norarginine", Tetrahedron Letters, vol. 37, No. 33, 1996, pp. 5839–5840.

Yong et al., "Facile and Efficient Guanylation of Amines Using Thioureas and Mukaiyama's Reagent",J. Org. Chem. vol. 62, 1997, pp. 1540–1542.

Drewry et al., "Solid–Phase Synthesis of Trisubstituted Guanidines", Tetrahedron Letters, vol. 38, No. 19, 1997, pp. 3377–3380.

Wang et al., "Solid–Phase Synthesis of 3,4–Dihydroquinazoline", Tetrahedron Letters, vol. 38, No. 50, 1997, pp. 8651–8654.

Kearney et al., "Solid–Phase Synthesis of Disubstituted Guanidines", Tetrahedron Letters, vol. 39, 1998, pp. 263–2666.

Dodd et al., "Solid–Phase Synthesis of N,N' Substituted Guanidines", Tetrahedron Letters, vol. 39, 1998, pp. 5701–5704.

Josey et al., "Novel Linker for the Solid–Phase Synthesis of Guanidines", Tetrahedron Letters, vol. 39, 1998, pp. 5899–5902.

Atwal et al., "A Facile Synthesis of Cyanoguanidines From Thioureas", Tetrahedron Letters, vol. 30, No. 52, 1989, pp. 7313–7316.

Kim et al., "Improved Method for the Preparation of Guanidines", Tetrahedron Letters, vol. 34, No. 48, 1993, pp. 7677–7680.

Levallet et al., "The $HgCl_2$–Promoted Guanylation Reaction: The Scope and Limitations", Tetrahedron, vol. 53, 1997, pp. 5291–5304.

Barvian et al., "Preparation of N,N'–Bis(aryl)guanidines from Electron Deficient Amines Via Masked Carbodiimides", Tetrahedron Letters, vol. 39, 1997, pp. 6799–6802.

Lorsbach et al., "Reissert–Based "Traceless" Solid–Phase Synthesis: Isoquilnoline, and Isoxazoline–Containing Heterocycles", J. Org. Chem., vol. 61, 1996, pp. 8716–8717.

Panek et al., "Synthesis of Aromatic 1,2–Diazines by Inverse Electron Demand Diels–Alder Reaction of Polymer–Supported 1,2,4,5–Tetrazines", Tetrahedron Letters, vol. 37, No. 45, 1996, pp. 8151–8154.

(List continued on next page.)

Primary Examiner—Brian J. Davis
(74) Attorney, Agent, or Firm—Richard S. Echler, Sr.; David V. Upite; Milton B. Graff, III

(57) ABSTRACT

The subject invention involves novel acyl isothiocyanate resins of formula (I) and processes for making them: (a) starting with a phenyl carboxy resin, treating the resin with any reagent that converts the carboxy to an acyl halide, followed by treatment with tetranikylammonium thiocyanate or an alkali metal salt thereof, to provide the acyl isothiocyanate resin. The subject invention also involves processes for making guanidine compounds and related cyclized compounds using an acyl isothiocyanate resin, comprising the following steps: (b) reacting the acyl isothiocyanate resin with a primary amine; (c) reacting the product from Step (b) with a sulfur activating agent and ammonia or a primary or secondary amine; (d) treating the product from Step (c) with a strong base or medium strength acid to cleave product from the resin, providing the guanidine compound or/and the related cyclized compound.

8 Claims, No Drawings

OTHER PUBLICATIONS

Schneider et al., "Solid Phase Synthesis of Oligomeric Guanidinuims", *Tetrahedron*, vol. 54, 1998, pp. 15063–15086.

Zhong et al., "Solid–Phase Synthesis of Arginine–Containing Peptides by Guanidine Attachment to a Sulfonyl Linker", *J. Org. Chem.*, vol. 62, 1997, pp. 9326–9330.

Messmer et al. "Synthesis and Structural Study of Azidonaphtho–as–triazines: "Annelation Effect" in Azide–Tetrazole Equlibria", *J. Org. Chem.*, vol. 49, 1984, pp. 3199–3203.

Aronov et al., "Phthalimide Resin Reagent for Efficient Mitxunobu Amino–Dehydroxylation", *Tetrahedron Letters*, vol. 39, 1998, pp. 4947–4950.

* cited by examiner

ACYL ISOTHIOCYANATE RESINS AND THEIR USE IN SOLID-SUPPORTED SYNTHESIS OF GUANIDINES

This application is a 371 of PCT/US99/29771 filed Dec. 15, 1999, which claims the benefit of Ser. No. 60/112,756, filed Dec. 17, 1998.

TECHNICAL FIELD

The subject invention relates to methods for synthesizing guanidine compounds, using a solid-support resin to facilitate purification of intermediates and compounds.

BACKGROUND OF THE INVENTION

Solid supported combinatorial chemistry methods have proven to be useful for small molecule based library construction. Substituted guanidine compounds are well known to be responsible for the basis of a variety of phannacological responses (e.g. anti-hypertensive, cardiotonic, $H_2$ antagonist/agonist, adrenoreceptor agonists, H+/K+ ATPase inhibition, NO synthase inhibition. anti-tumor activity), and there are several examples which have resulted in marketed drug substances.

Examples of guanidine synthesis processes are disclosed in the following references: Robinson, S.; Roskamp, E. J. TetrahedronLett. 1997, 53(19), 6697–6705; Yong, Y. F.; Kowalski, J. A.; Lipton. M. A. J. Org. Chem. 1997, 62, 1540–1542; Kowalski, J.; Lipton, M. A. TetrahedronLett. 1996, 37(33), 5839–5840; Drewry, D. H.; Gerritz, S. W.; Linn, J. A. TetrahedronLett. 1997. 38(19), 337–3380; Wang, F.; Hauske, J. R. TetrahedronLett. 1997, 38, 8651–8654; Kearney, P. C.; Fernandez, M.; Flygare, J. A. Tetrahedron-Lett. 1998, 39, 2663–2666; Dodd, D. S.; Wallace, O. B. TetrahedronLett. 1998, 39, 5701–5704; Josey, J. A.; Tarlton, C. A.; Payne, C. E. TetrahedronLett. 1998, 39, 5899–5902; Stephensen, H.; Zaragoza, F. J. Org. Chem. 1997, 62, 6096–6097. Similar solution phase guanidine chemistries: Atwal, K. S.; Ahimed, S. Z.; O'Reilly, B. C. Tetrahedron-Lett. 1989, 30 (52), 7313–7316; Poss, M. A.; Iwanowicz, E.; Reid, J. A.; Lin, J.; Gu, Z. TetrahedronLett. 1992, 33 (40), 5933–5936; Kim, K. S.; Qian, L. TetrahedronLett. 1993, 34 (48), 7677–7680; Levallet, C.; Lerpiniere, J.; Ko, S. Y. Tetrahedron 1997, 53, 5291–5304; Barvian, M. R.; Showalter, H. D. H.; Doherty, A. M. TetrahedronLett. 1997, 38 (39), 6799–6802.

Examples of resin preparations are disclosed in the following references: Lorsbach, B. A.; Miller, R. B.; Kurth, M. J. J. Org. Chem. 1996, 61, 8716–8717; Panek, J. S.; Zhu, B. TetrahedronLett. 1996, 37(45), 8151–8154.

OBJECTS OF THE INVENTION

It is an object of the subject invention to provide processes for making guanidine compounds that would be general enough to provide access to a variety of different types in this series and take advantage of the large number of commercially available and diverse amine-based building blocks in both aliphatic and aromatic categories via a traceless linker strategy.

SUMMARY OF THE INVENTION

The subject invention involves processes for making guanidine compounds:

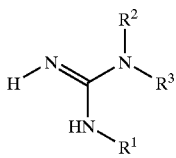

(1)

and related cyclized compounds:

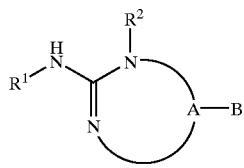

(8)

using a solid-support resin, comprising the following steps:

(b) reacting an acyl isothiocyanate resin:

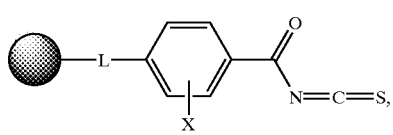

(2)

with a primary amine:

$R^1$—$NH_2$, (3)

wherein $R^1$ is selected from —R, —C(O)R, —$CO_2$R, —C(O)NHR, —C(O)$NR_2$, NHR, and $NR_2$, to provide:

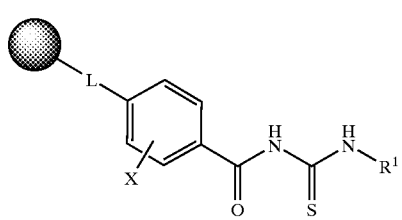

(6)

(c) reacting the product from Step (b) with a sulfur activating agent and ammonia or a primary or secondary amine:

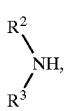

(4)

wherein R2 and R3 are each independently selected from hydrogen, alkyl, aryl, and heterocycle, to provide:

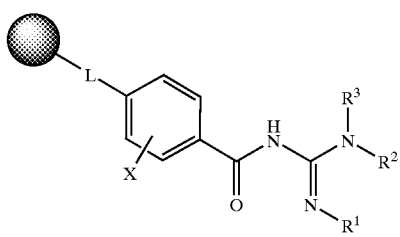

(7)

or, if R³ contains a displaceable group:

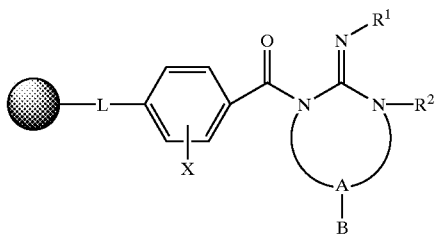

(9)

wherein

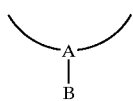

is derived from R³, A being selected from alkylene, arylene, and alkarylene, and B being, nil or one or more non-hydrogen substituents selected from —R, —OH, —OR, —SH, —SR, —NH₂, —NHR, —NR₂, =O, and =S; wherein, in Steps (a), (b), and (c), R is alkyl, aryl or heterocycle;

(d) treating the product from step (c) with a strong base or medium strength acid to cleave product from the resin, providing the guanidine compound or/and the related cyclized compound.

The subject invention also involves novel acyl isothiocyanate resins and processes for preparing them.

DETAILED DESCRIPTION OF INVENTION

As used herein unless specified otherwise, "alkyl" means a hydrocarbon chain which is branched, linear or cyclic, saturated or unsaturated (but not aromatic), substituted or unsubstituted. The term "alkyl" may be used alone or as part of another word where it may be shortened to "alk" (e.g., in alkoxy, alkylacyl). Preferred linear alkyl have from one to about twenty carbon atoms, more preferably from one to about ten carbon atoms, more preferably still from one to about six carbon atoms, still more preferably from one to about four carbon atoms; most preferred are methyl or ethyl. Preferred cyclic and branched alkyl have from three to about twenty carbon atoms, more preferably from three to about ten carbon atoms, more preferably still from three to about seven carbon atoms, still more preferably from three to about five carbon atoms. Preferred cyclic alkyl have one hydrocarbon ring, but may have two, three, or more, fused, spiro, or bridged hydrocarbon rings. Preferred alkyl are unsaturated with from one to about three double or triple bonds, preferably double bonds; more preferably they are mono-unsaturated with one double bond. Still more preferred alkyl are saturated. Saturated alkyl are referred to herein as "alkanyl". Alkyl unsaturated only with one or more double bonds (no triple bonds) are referred to herein as "alkenyl". Preferred substituents of alkyl include halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides, nitro, and cyano. Also, unsubstituted alkyl are preferred.

As used herein, "heteroatom" means a nitrogen, oxygen, or sulfur atom.

As used herein, "alkylene" means an alkyl which connects two other moieties, "heteroalkylene" means an alkylene having one or more heteroatoms in the connecting chain.

As used herein unless specified otherwise, "aryl" means an aromatic hydrocarbon ring (or fused rings) which is substituted or unsubstituted. The term "aryl" may be used alone or as part of another word (e.g., in aryloxy, arylacyl). Preferred aryl have from six to about fourteen, preferably to about ten, carbon atoms in the aromatic ring(s), and a total of from about six to about twenty, preferably to about twelve, carbon atoms. Preferred aryl is phenyl or naphthyl; most preferred is phenyl. Preferred substituents of aryl include halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides, nitro, and cyano. Also, unsubstituted aryl are preferred.

As used herein unless specified otherwise, "heterocycle" means a saturated, unsaturated or aromatic cyclic hydrocarbon ring (or fused, spiro, or bridged rings) with one or more heteroatoms in the hydrocarbon ring(s). Preferred heterocycles have from one to about six heteroatoms in the ring(s), more preferably one or two or three heteroatoms in the ring(s). Preferred heterocycles have from three to about fourteen, preferably to about ten, carbon plus heteroatoms in the ring(s), more preferably from three to about seven, more preferably still five or six, carbon plus heteroatoms in the ring(s); and a total of from three to about twenty carbon plus heteroatoms, more preferably from three to about ten, more preferably still five or six, carbon plus heteroatoms. Preferred heterocycles have one ring, but may have two, three, or more, fused spiro, or bridged rings. More preferred heterocycle rings include those which are one ring with 5 or 6 carbon plus heteroatoms in the ring with no more than three ring heteroatoms, no more than two of which are O and S. Still more preferred are such 5- or 6-ring atom heterocycles with one or two ring atoms being O or S and the others being C; or with one, two or three ring atoms being N and the others being C. Such preferred 5- or 6-ring atom heterocycles are preferably saturated, unsaturated with one or two double bonds, or aromatic. Such preferred 5- or 6-ring atom heterocycles are preferably a single ring; or fused with a 3- to 6-ring atom hydrocarbon ring which is saturated, unsaturated with one double bond, or aromatic (phenyl); or fused with another such 5- or 6-ring atom heterocyclic ring. Heterocycles are unsubstituted or substituted. Preferred heterocycle substituents are the same as for alkyl.

The subject invention involves acyl isothiocyanate resins having the structure:

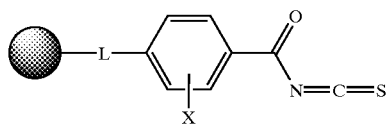

(2)

In structure (2), —L— is a single bond or a linking moiety. Preferred linking moieties have the structures —Ph—CH$_2$—(OCH$_2$CH$_2$)$_n$—O—, where Ph is phenyl, and n is from 0 to about 100. A preferred linking moiety is —Ph—CH$_2$O—. More preferred is —L— being a single bond.

In structure (2), —X designates non-hydrogen, mono- or disubstituents on the phenyl ring. Preferred non-hydrogen substituents include alkyl, alkoxy, alkylthio, halo, and nitro; more preferred is methoxy. Especially preferred is no non-hydrogen —X substituents on the phenyl ring.

Acyl isothiocyanate resin (2) is preferably prepared using Step (a) which starts with a resin having the structure:

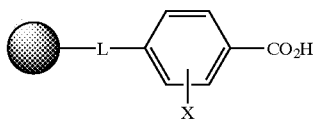

(5)

In structure (5), —L— and —X are as defined previously. Highly preferred resin starting materials are carboxy polystyrene resins, such as carboxypolystyrene, available from Advanced Chemtech, Louisville, Ky.

Step (a) of the subject invention processes involves treating the starting resin with any reagent that converts the carboxy moieties to acyl halide moieties. Preferred reagents for achieving this conversion are oxalyl chloride plus dimethylformamide (DMF). This conversion is preferably carried out in a chlorinated solvent, such as dichloromethane (DMC), chloroform, and especially 1,2-dichloroethane (DCE).

The converted resin is then treated with tetraalkylammonium thiocyanate, or an alkali metal salt thereof, to provide acyl isothiocyanate resin:

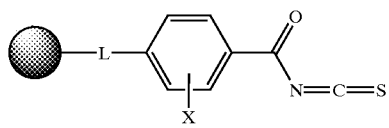

(2)

The tetraalkylammnonium thiocyanate preferably has alkyl moieties having from about 1 to about 18 carbon atoms, more preferably from about 2 to about 8 carbon atoms; especially preferred is tetrabutylammonium thiocyanate (Bu$_4$NNCS). This reaction is preferably carried out in tetrahydrofuran (THF) solvent or a mixture of THF and a chlorinated solvent; especially preferred is a solvent mixture of about 1:1 THF and 1,2-DCE.

Step (b) of the subject invention processes involves reacting the acyl isothiocyanate resin with a primary amine:

$R^1$—NH$_2$ (3), to provide:

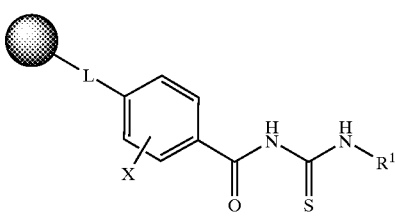

(6)

In structures (3) and (6), $R^1$ is a non-hydrogen moiety, preferably selected from —R, —C(O)R, —CO$_2$R, —C(O)NHR, —C(O)NR$_2$, —NHR, —NR$_2$ wherein R is alkyl, aryl or heterocycle. More preferred $R^1$ include alkyl, aryl, and heterocycle. Preferred alkyl $R^1$ include alkyl having from 1 to about 8 carbon atoms, more preferably from 1 to about 4 carbon atoms; such alkyl are preferably unsubstituted or substituted with phenyl or a heterocycle ring having 5 or 6 ring atoms. Preferred aryl $R^1$ are unsubstituted and substituted phenyl. Preferred heterocycle $R^1$ are unsubstituted and substituted heterocycle rings having 5 or 6 ring atoms, of which 1, 2 or 3 are heteroatoms.

The reaction of Step (b) is preferably carried out in dimethylforrnamide (DMF) solvent, chlorinated solvents, or combinations of chlorinated and DMF-type solvents, such as N-methylpyrrolidinone or N,N-dimethylacetamide. The preferred solvent is DMF.

In Step (c) of the subject invention processes, the product from Step (b) is reacted with a sulfur activating agent and ammonia or a primary or secondary amine:

$$R^2\diagdown NH \atop R^3\diagup$$ (4)

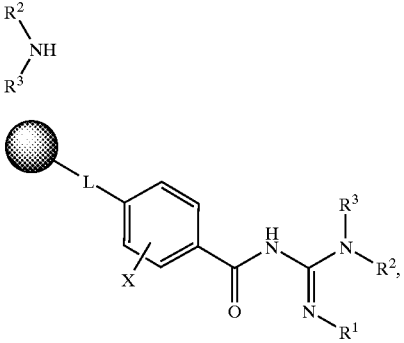

(7)

to provide:
or, if $R^3$ contains a displaceable group:

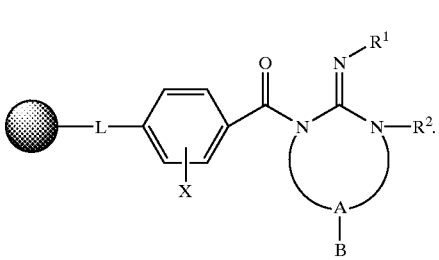

(9)

In structures (4), (7) and (9), $R^2$ and $R^3$ are each independently selected from hydrogen, alkyl, aryl, heterocycle, or $R^2$ and $R^3$ are connected to form, with the nitrogen to which both are attached, a heterocyclic ring. Preferred $R^2$ and $R^3$ include hydrogen. Preferred alkyl $R^2$ and $R^3$ are unsubstituted or substituted alkyl having from 1 to about 8 carbon atoms, more preferably from 1 to about 4 carbon atoms. Preferred aryl $R^2$ and $R^3$ include unsubstituted or substituted phenyl. Preferred heterocycle $R^2$ and $R^3$ include unsubstituted or substituted heterocycle rings having 5 or 6 ring atoms, of which 1, 2 or 3 are hetero atoms.

Examples of displaceable groups for $R^3$, such that structure (9) is produced in Step (c), include hydroxy that can react in a Mitsunobu reaction, alkyl chlorides, esters, and activated carboxylic acids.

In structure (9), A is preferably selected from alkylene, arylene, and alkarylene. A preferably has 2 or 3 or 4 atoms linearly connected between the two nitrogens to which it connects, thus forming a 5 or 6 or 7 atom heterocylic ring with these two nitrogen atoms and the carbon to which both of them are connected.

In structure (9), B is preferably nil or 1 or more non-hydrogen substituents selected from —R, —OH, —OR, —SH, —SR, —NH$_2$, —NHR, —NR$_2$, =O, and =S, wherein R is alkyl, aryl or heterocycle.

The sulfur activating agent used is Step (c) is any agent which converts the S in structure (6) into a good leaving group. Preferred sulfur activating agents include ethyldiaminopropylcarbodiimide.HCl (EDC), diisopropylcarbodiimide (DIC), 1-Me-2-Cl-pyridinium iodide (Murikyama's agent), tetra-Me-F-uronium-tetra-F-borate salt. The most preferred sulfur activating agent is EDC. Preferred solvents in which Step (c) is carried out include DMF, chloroform, and mixtures of these two.

Step (d) of the subject invention processes involves treating the product from Step (c) with a strong base or a medium strength acid to cleave product from the resin, providing the guanidine compound:

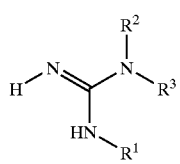

(1)

or/and the related cyclized compound:

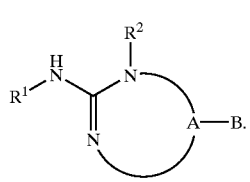

(8)

Sometimes cyclization occurs during Step (d). Preferred reagents for achieving such cleavage include hydrazine, trifluoroacetic acid (TFA), mineral acids such as hydrochloric acid, and sodium methoxide; more preferred reagents are hydrazine and TFA. Step (d) is preferably carried out in a solvent which is a mixture of methanol or ethanol and a chlorinated solvent; most preferred is a solvent which is about 1:1 chloroform and methanol.

The following general scheme depicts preferred processes of the subject invention:

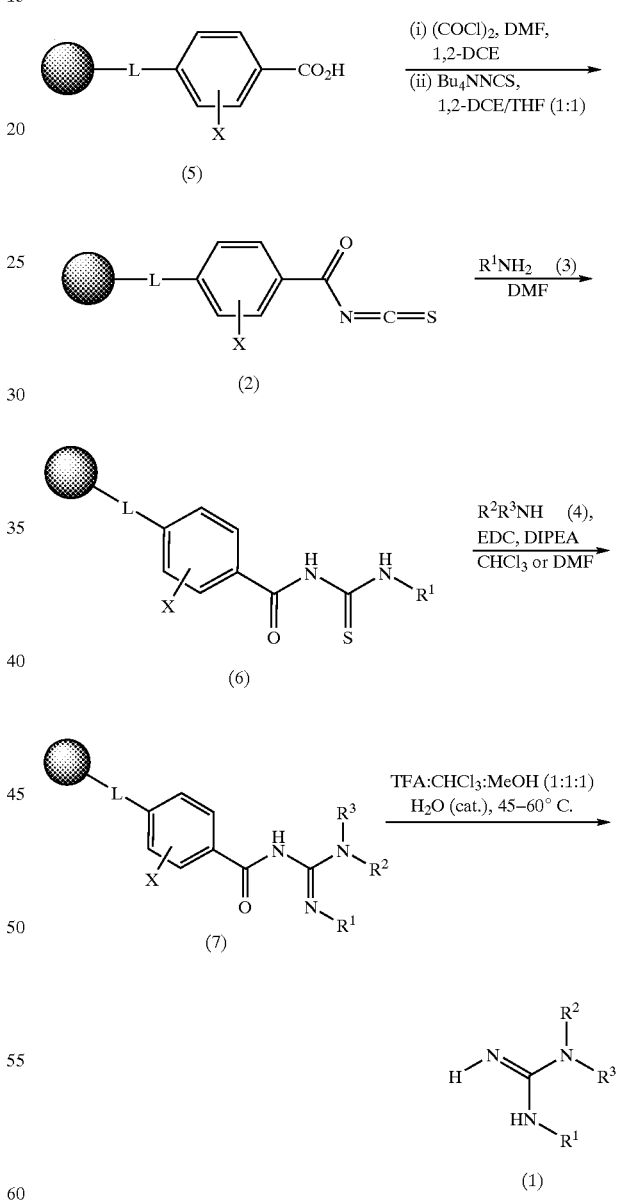

The reagents, reaction conditions, and solvents depicted in the above scheme are used to prepare Examples A–H shown in the following table:

| Example | R¹NH₂ (3) | R²R³NH (4) | Guanidine (1)[a] |
|---|---|---|---|
| A | 3-iodobenzylamine | NH₃ | N-(3-iodobenzyl)guanidine |
| B | 1-benzyl-4-aminopiperidine | NH₃ | N-(1-benzylpiperidin-4-yl)guanidine |
| C | 2,6-dichloroaniline | NH₃ | N-(2,6-dichlorophenyl)guanidine |
| D | aniline | 1,2,3,4-tetrahydroisoquinoline | N-phenyl-3,4-dihydroisoquinoline-2(1H)-carboximidamide |
| E | cyclohexylamine | 1,2,3,4-tetrahydroisoquinoline | N-cyclohexyl-3,4-dihydroisoquinoline-2(1H)-carboximidamide |
| F | 4-iodoaniline | 1-adamantanamine | N-(4-iodophenyl)-N'-(1-adamantyl)guanidine |
| G | aniline | aniline | N,N'-diphenylguanidine |
| H | 2-morpholinoaniline | Me₂NH | N-(2-morpholinophenyl)-N',N'-dimethylguanidine |

[a]Isolated as the trifluoroacetic acid salts.

For the above examples, the acyl isothiocyanate resin is prepared as follows: 850 mg of carboxypolystryene (Advanced Chemtech, Louisville, Ky.; loading=0.7 mmol/g) is swelled with anhydrous 1,2-DCE (2×10 mL), followed by the addition of 10 mL of 1,2-DCE, 0.5 mL of DMF, and 0.75 mL of oxalyl chloride/DCM solution (added slowly over 5 minutes; 2M, Aldrich). After initial bubbling has subsided the vessel is agitated for 8 hours. After filtration, this is repeated again overnight (14 hours). The resin is washed with 1,2-DCE (3×10 mL), and charged with Bu₄NNCS in 1,2-DCE/THF (1:1) solution (1.2 g in 10 mL), followed by shaking for 4 hours. This is repeated for another 5 hours, and the resin is washed (3×10 mL of THF; 3×10 mL of 1,2-DCE), followed by drying under nitrogen.

While particular embodiments of the subject invention have been described, it will be obvious to those skilled in the arts that various changes and modifications of the subject invention can be made without departing from the spirit and scope of the invention. It is intended to cover, in the appended claims, all such modifications that are within the scope of this invention.

What is claimed is:

1. A process for making guanidine compounds:

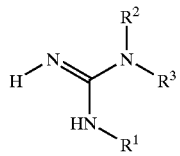

and related cyclized compounds:

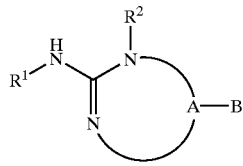

using a solid-support resin, comprising the following steps:

(b) reacting an acyl isothiocyanate resin

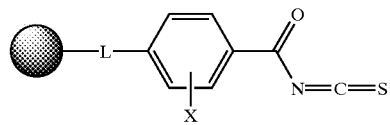 (I)

wherein —L— is a linking moiety, and —X is nil or one or two non-hydrogen substituents independently selected from alkyl, alkoxy, alkylthio, halo, and nitro, with a primary amine:

$R^1$—NH$_2$, wherein $R^1$ is selected from —R, —C(O)R, —CO$_2$R, —C(O)NHR, —C(O)NR$_2$, —NHR, —NR$_2$, wherein R is selected from alkyl, aryl, and heterocycle, to provide:

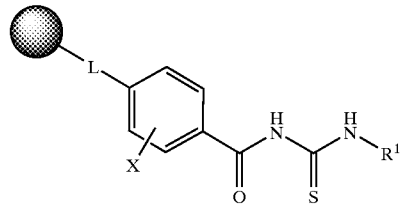

(c) reacting the product from Step (b) with a sulfur activating agent and ammonia or a primary or secondary amine:

wherein R2 and R3 are each independently selected from hydrogen, alkyl, aryl, and heterocycle, to provide:

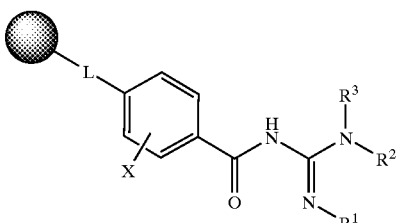

or, if $R^3$ contains a displaceable group:

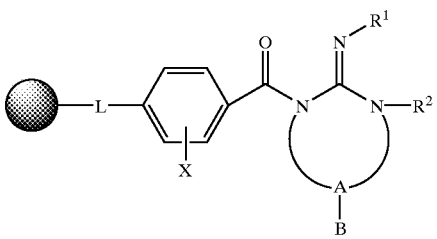

wherein

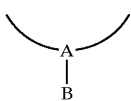

is derved from $R^3$, A being selected from alkylene, arylene, and alkarylene, and B being nil or one or more non-hydrogen substituents selected from —R, —OH, —OR, —SH, —SR, —NH$_2$, —NHR, —NR$_2$, =O, and =S, wherein R is selected from alkyl, aryl and heterocycle;

(d) treating the product from Step (c) with a strong base or medium strength acid to cleave product from the resin, providing the guanidine compound or/and the related cyclized compound.

2. The process of claim 1 wherein the acyl isothiocyanate resin is prepared by the following process:

(a) starting with a phenyl carboxy resin:

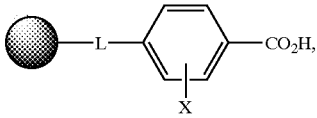

treating the resin with any reagent that converts the carboxy moieties of the resin to acyl halide, followed by treatment with tetraalkylammonium thiocyanate or an alkali metal salt thereof, to provide the acyl isothiocyanate resin.

3. The process of claim 2 wherein —L— is a single bond or —Ph—CH$_2$—(OCH$_2$CH$_2$)$_n$—O—, and n is an integer from 0 to 100.

4. The process of claim 3 wherein the reagents used in Step (a) to convert the carboxy moieties of the resin to acyl halide are oxalyl chloride plus dimethylformamide, and wherein the tetraalkylammonium thiocyanate used in Step (a) is tetrabutylammonium thiocyanate.

5. The process of claim 4 wherein $R^1$ is selected from unsubstituted or substituted alkyl having from 1 to 8 carbon atoms; unsubstituted or substituted phenyl; and unsubstituted or substituted heterocycle rings having 5 or 6 ring atoms, of which 1, 2 or 3 are heteroatoms.

6. The process of claim 5 wherein $R^2$ and $R^3$ are each independently selected from hydrogen, unsubstituted or substituted alkyl having from 1 to 8 carbon atoms, unsubstituted or substituted phenyl; and unsubstituted or substituted heterocycle rings having 5 or 6 ring atoms, of which 1, 2 or 3 are heteroatoms; or $R^2$ and $R^3$ are connected to form, with the nitrogen to which both are attached, an unsubstituted or substituted heterocycle ring having 5 or 6 ring atoms, of which 1, 2, or 3 are heteroatoms, and wherein in Step (c), the following structure is formed:

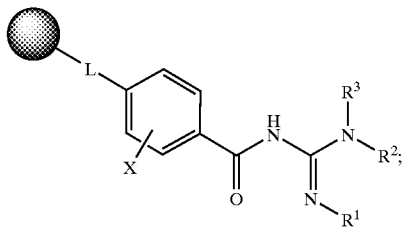

or $R^2$ is selected from hydrogen, unsubstituted or substituted alkyl having from 1 to 8 carbon atoms, unsubstituted or substituted phenyl, and unsubstituted or substituted heterocycle rings having 5 or 6 ring atoms, of which 1, 2 or 3 are heteroatoms, and $R^3$ is a displaceable group selected from hydroxy, alkyl chloride, and carboxylic acid, wherein, in Step (c) the following structure is formed:

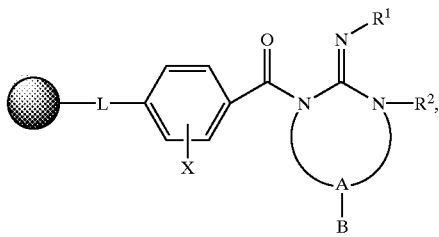

wherein A is selected form alkylene, phenylene, and alkphenylene, whereby 2, 3 or 4 carbon atoms are connected between the two nitrogens to which —A— is connected, and —B is nil or one or two non-hydrogen substituents independently selected from —R, —OH, —OR, —SH, —SR, —$NH_2$, —NHR, —$NR_2$, =O, and =S, wherein —R is selected from unsubstituted or substituted alkyl having from 1 to 8 carbon atoms, unsubstituted or substituted phenyl, and unsubstituted or substituted heterocycle rings having 5 or 6 ring atoms, of which 1, 2 or 3 are heteroatoms.

7. The process of claims 6 wherein in Step (c) the sulfur activating agent is selected from ethyldiaminopropylcarbodiimide, diisopropylcarbodiimide, 1-methyl-2-chloro-pyridinium iodide, and tetramethyl-fluoro-uronium-tetrafluoro-borate salt; and in Step (d), the strong base or medium strength acid is selected from hydrazine, trifluoroacetic acid, hydrochloric acid, and sodium methoxide.

8. A process for making an acyl isothiocyanate resin having the structure:

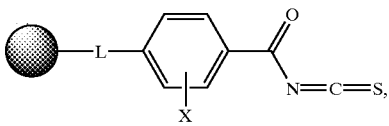

wherein —L— is a single bond or a linking moiety, and —X is nil or one or two non-hydrogen substituents selected from alkyl, alkoxy, alkylthio, halo, and nitro comprising:

(a) starting with a phenyl carboxy resin:

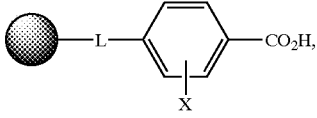

treating the resin with any reagent that converts the carboxy moieties of the resin to acyl halide, followed by treatment with tetraalkylammonium thiocyanate or an alkali metal salt thereof to provide the acyl isothiocyanate resin.

* * * * *